US010073040B2

(12) United States Patent
Miyamoto et al.

(10) Patent No.: US 10,073,040 B2
(45) Date of Patent: Sep. 11, 2018

(54) METHOD FOR DETECTING NUCLEIC ACID, AND DEVICE OR KIT

(71) Applicant: Kaneka Corporation, Osaka (JP)

(72) Inventors: Shigehiko Miyamoto, Hyogo (JP); Tomohisa Kato, Hyogo (JP); Koji Takahashi, Hyogo (JP); Jun Tomono, Hyogo (JP)

(73) Assignee: KANEKA CORPORATION, Osaka (JP)

( * ) Notice: Subject to any disclaimer, the term of this patent is extended or adjusted under 35 U.S.C. 154(b) by 0 days.

(21) Appl. No.: 13/768,143

(22) Filed: Feb. 15, 2013

(65) Prior Publication Data

US 2013/0143224 A1 Jun. 6, 2013

Related U.S. Application Data

(62) Division of application No. 12/726,680, filed on Mar. 18, 2010, now Pat. No. 8,546,131.

(60) Provisional application No. 61/248,921, filed on Oct. 6, 2009.

(30) Foreign Application Priority Data

Mar. 19, 2009 (JP) ................. 2009-068181
Jun. 15, 2009 (JP) ................. 2009-142468
Jul. 29, 2009 (JP) ................. 2009-176784
Jul. 29, 2009 (JP) ................. 2009-176785

(51) Int. Cl.
*G01N 21/78* (2006.01)
*C12Q 1/6816* (2018.01)
*G01N 33/52* (2006.01)
*G01N 33/53* (2006.01)

(52) U.S. Cl.
CPC ........... *G01N 21/78* (2013.01); *C12Q 1/6816* (2013.01); *G01N 33/52* (2013.01); *G01N 33/5308* (2013.01)

(58) Field of Classification Search
USPC .................. 435/6.1, 6.11, 91.1; 436/94, 501; 536/23.1, 24.3
See application file for complete search history.

(56) References Cited

U.S. PATENT DOCUMENTS

| 4,851,353 A * | 7/1989 | Miike ...................... C12Q 1/28 422/421 |
| 5,229,297 A | 7/1993 | Schnipelsky et al. |
| 5,326,388 A * | 7/1994 | Miller ...................... B05D 1/36 106/31.32 |
| 5,496,677 A | 3/1996 | Toyama et al. |
| 6,194,560 B1 * | 2/2001 | Arntzen et al. .............. 536/23.7 |
| 7,226,719 B2 * | 6/2007 | Wisnudel et al. ....... 430/270.11 |
| 8,481,331 B2 * | 7/2013 | Cregger .................. C09B 21/00 422/50 |
| 2003/0138824 A1 | 7/2003 | Makino et al. |
| 2004/0171016 A1 | 9/2004 | Tomita et al. |
| 2010/0136012 A1 * | 6/2010 | Keshet ................. G01N 33/689 424/139.1 |

FOREIGN PATENT DOCUMENTS

| EP | 1416055 A1 | 5/2004 |
| JP | 54145596 A | 11/1979 |
| JP | 5237000 A | 9/1993 |
| JP | H-05507362 A | 10/1993 |
| JP | 06-022796 A | 2/1994 |
| JP | 06197797 A | 7/1994 |
| JP | 08-054746 A | 2/1995 |
| JP | 08-248652 A | 9/1996 |
| JP | 9187275 A | 7/1997 |
| JP | 2001-075271 | 3/2001 |
| JP | 2001-299386 A | 10/2001 |
| JP | 2001-521622 A | 11/2001 |
| JP | 2002186481 A | 7/2002 |
| JP | 2002-291499 A | 10/2002 |
| JP | 2003-144152 A | 5/2003 |
| JP | 2003-61658 A | 9/2004 |
| JP | 2006-149215 A | 6/2006 |
| KR | 10-0161276 B1 | 11/1998 |
| WO | WO-0166688 A1 | 9/2001 |
| WO | WO-02/10305 A1 | 12/2002 |

(Continued)

OTHER PUBLICATIONS

Acid-Base indicators. Printed on Oct. 1, 2013.*
Bassam et al., Protocols in Biotechnology, Silver Staining of DNA in polyacrylamide Gels. Applied Biochemistry and Biotechnology, 42, 181-188, 1993.*
The definition for "dye". Printed on Oct. 4, 2013.*
"Methylene blue" from Wikipedia, the free encyclopedia. Printed on Sep. 5, 2014.*
"Pyronin Y" from Sigma-Aldrich. Printed on Feb. 2, 2017.*
The English translation fo the International Search Report issued in related International Application No. PCT/JP2010/054350 dated Jun. 1, 2010.

(Continued)

*Primary Examiner* — Frank Wei Min Lu
(74) *Attorney, Agent, or Firm* — Polsinelli PC

(57) ABSTRACT

A method and a device or kit for detecting a nucleic acid, which enable simple and precise visual detection of a nucleic acid amplified by an nucleic acid amplification method, without necessity of special devices are provided. The method for detecting a nucleic acid in a sample comprises: contacting a sample with a dye to react with each other; and observing a substance produced by the reaction with visible light, and evaluating the presence or absence of a nucleic acid by eye. The device or kit for detecting a nucleic acid in a sample comprises: a carrier that holds a dye which can bind to a nucleic acid; a path for passing a sample through the carrier; and an evaluation part for observing a substance produced by the reaction between the sample and the dye with visible light, and evaluating the presence or absence of a nucleic acid by eye.

4 Claims, 4 Drawing Sheets

Specification includes a Sequence Listing.

(56) References Cited

FOREIGN PATENT DOCUMENTS

WO    WO-2002/103053 A1    12/2002

OTHER PUBLICATIONS

The English language translation of the International Preliminary Report on Patentability and Written Opinion as issued in related International Application No. PCT/JP2010/054350 dated Oct. 18, 2011.

"Peroxidase" from calzyme.com. printed on Aug. 7, 2012.

"Ethidium bromide" from Wikipedia, the free encyclopedia. Printed on Feb. 8, 2012.

Prento et al., Methyl green-pyronin Y straining of nucleic acids: studies on the effects of staining time, dye composition and diffusion rates. Biotechnic & Histochemistry, 78, 27-33, 2003.

"Reducing agent" and "peroxidase" from Wikipedia, the free encyclopedia. Prined on Feb. 8, 2012.

Glynou et al., "Oligonucleotide-Functionalized Gold Nanoparticles as Probes in a Dry-Reagent Strip Biosensor for DNA Analysis by Hybridization", Analytical Chemistry, vol. 75, No. 16, Aug. 15, 2003, pp. 4155-4160.

Baeumner et al., "A Universal Nucleic Acid Sequence Biosensor with Nanomolar Detection Limits," Analytical Chemistry, vol. 76, No. 4, Feb. 15, 2004, pp. 888-894.

Hanafi-Bagby et al., "Concentration Dependence of a Thiazole Orange Derivative That is Used to Determine Nucleic Acid Hybridization by an Optical Biosensor," Analytica Chimica Acta, vol. 411, Jan. 2000, pp. 19-30.

Hill et al., "Loop-Mediated Isothermal Amplification Assay for Rapid Detection of Common Strains of *Escherichia coli*", Journal of Clinical Microbiology, Aug. 2008, p. 2800-2804.

Prento et al., "Methyl green-pyronin Y staining of nucleic acids: studies on the effects of staining time, due composition and diffusion rates", Biotechnic & Histochemistry, 2003, vol. 78, No. 1, p. 27-33.

R.E. Farrell, Jr., Rna Methodologies: A Laboratory Guide for Isolation and Characterization, 3rd Edition 2008, p. 119-123 in chinese.

Sambrook, Molecular Cloning: A Laboratory Manual, 3rd Edition, vol. II, Appendix 1, Science Press, Aug. 2002, pp. 1565-1594 in chinese.

\* cited by examiner

[Figure 1]
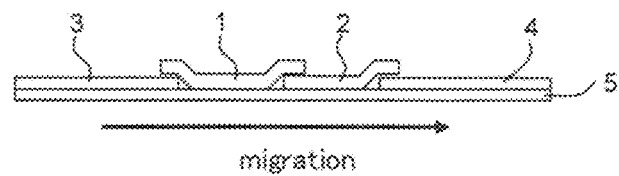
migration
[Figure 2]
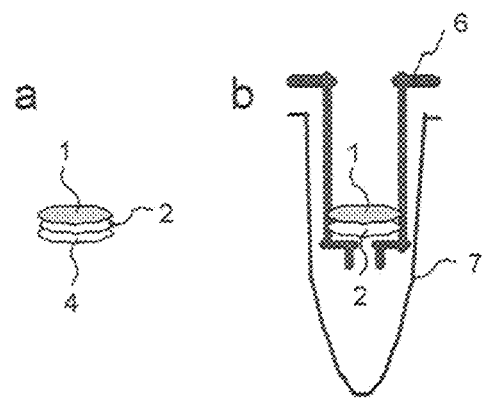
[Figure 3]
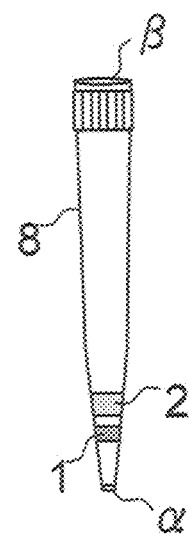

[Figure 4]
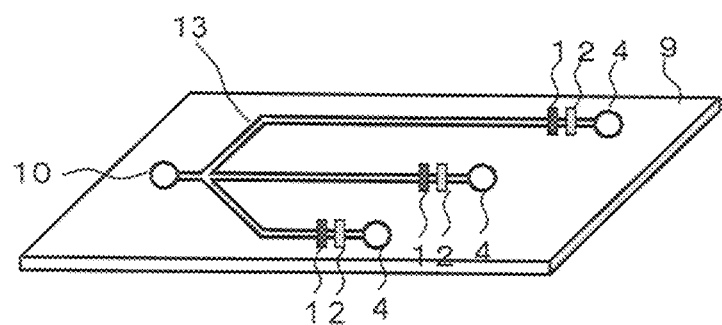
[Figure 5]
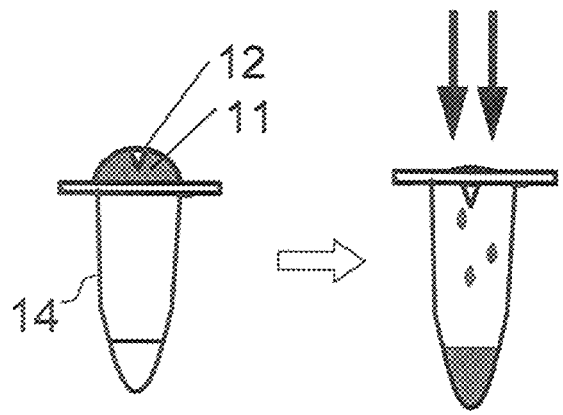

[Figure 6]
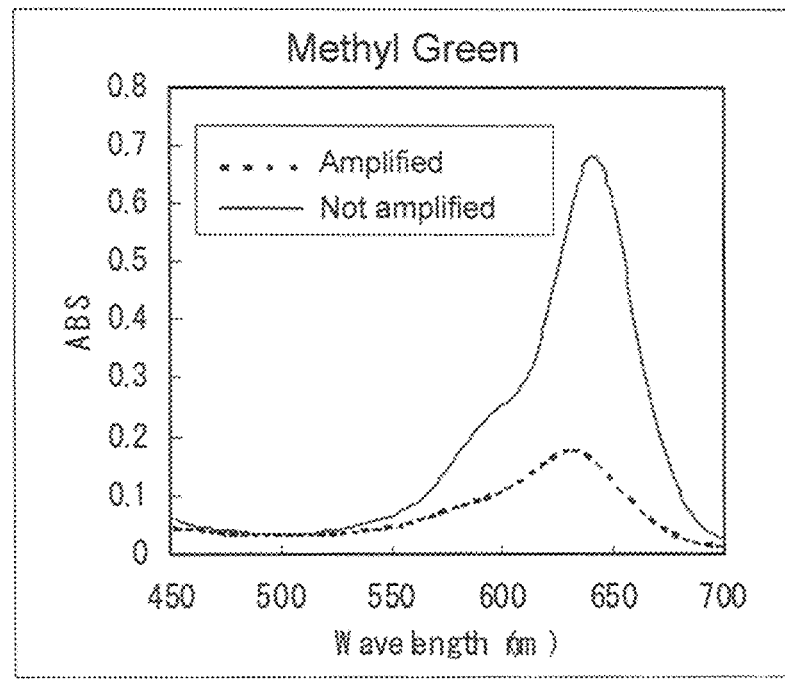
[Figure 7]
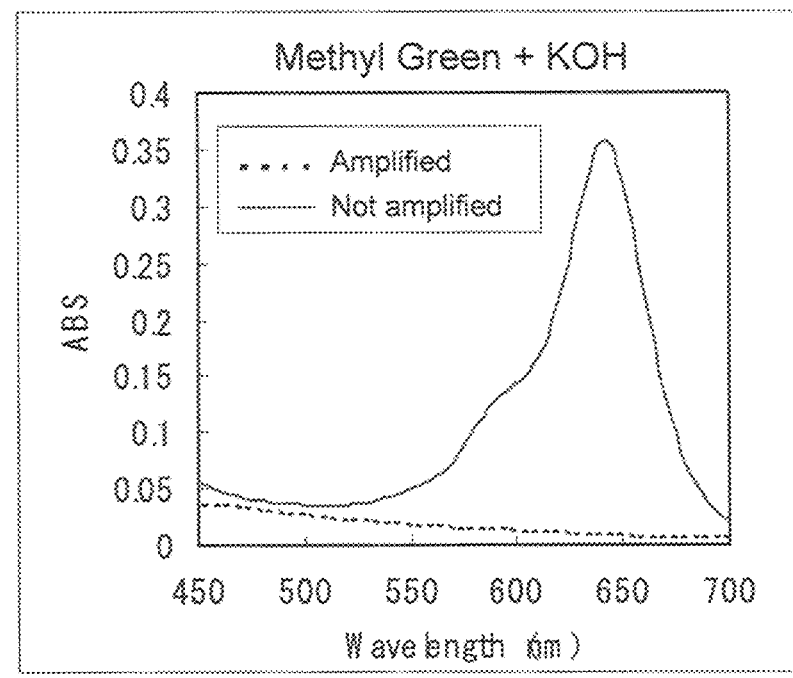

[Figure 8]
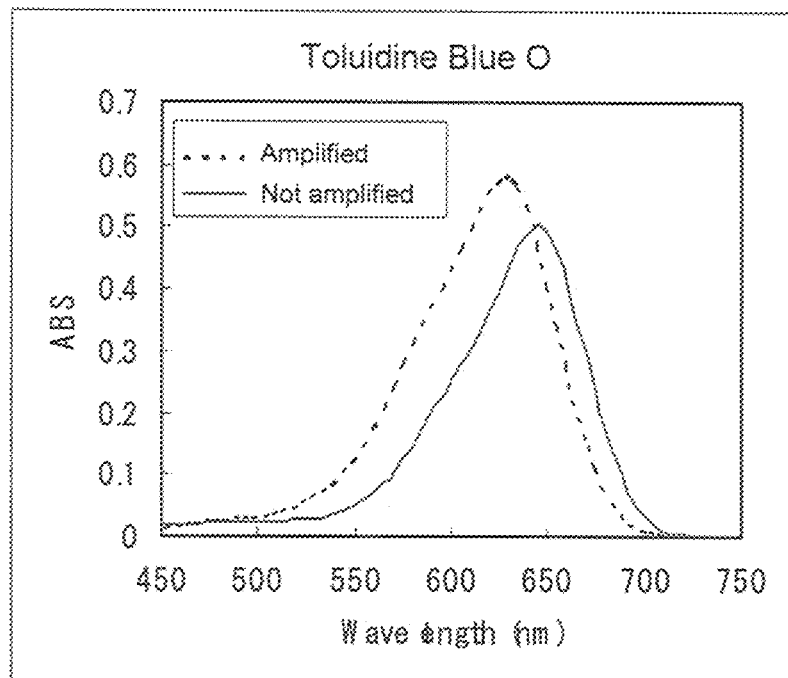
[Figure 9]
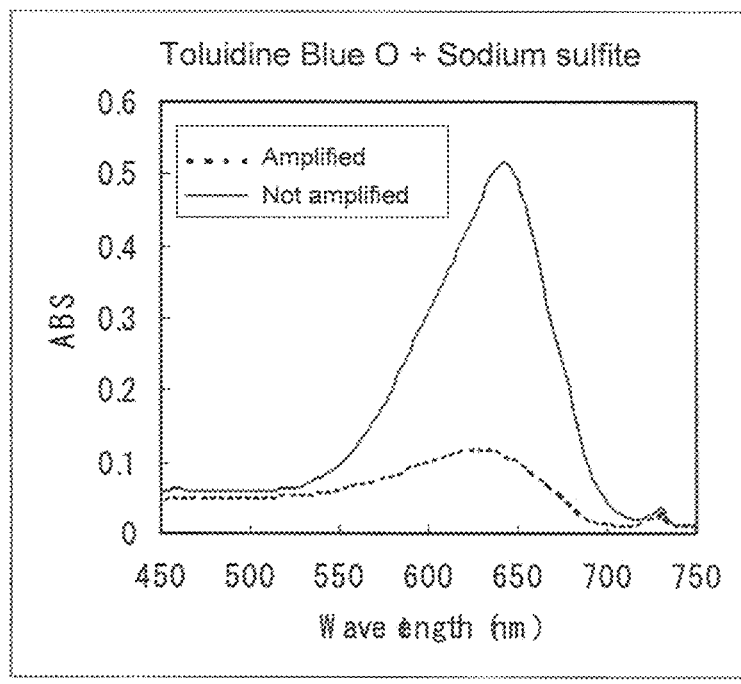

METHOD FOR DETECTING NUCLEIC ACID, AND DEVICE OR KIT

CROSS REFERENCE TO RELATED APPLICATIONS

This application is a Divisional of application Ser. No. 12/726,680, filed on Mar. 18, 2010, now U.S. Pat. No. 8,546,131 B2; and this application claims priority to Application No. 2009-068181 filed in Japan on Mar. 19, 2009, Application No. 2009-142468 filed in Japan on Jun. 15, 2009, Application No. 2009-176784 filed in Japan on Jul. 29, 2009, and Application No. 2009-176785 filed in Japan on Jul. 29, 2009; and this application claims the benefit of U.S. Provisional Application No. 61/248,921 filed on Oct. 6, 2009; the entire contents of all are hereby incorporated by reference.

SUBMISSION OF SEQUENCE LISTING

The Sequence Listing associated with this application is filed in electronic format via EFS-Web and hereby incorporated by reference into the specification in its entirety. The name of the text file containing the Sequence Listing is 21581_510_US_Seq_List. The size of the text file is 1 KB, and the text file was created on Jan. 10, 2011.

TECHNICAL FIELD

The present invention relates to a method, a kit and device for detecting a nucleic acid, which enable detection of a nucleic acid amplified by a nucleic acid amplification method.

BACKGROUND ART

In the research field of molecular biology, and clinical application field such as genetic testing, a method for specifically amplifying the target nucleic acid piece has been a very important technology. Examples of such a gene amplification method include developing isothermal amplification methods, such as LAMP (Loop-Mediated Isothermal Amplification) method and ICAN (Isothermal and Chimeric primer-initiated Amplification of Nucleic acids) method, in addition to the most general PCR method (Polymerase Chain Reaction).

The method for detecting the specific nucleic acid region amplified by a method such as PCR method, LAMP method, or ICAN method can be classified into two methods: a method for detecting DNA, an amplification product; and a method for detecting a pyrophosphoric acid (diphosphoric acid), a by-product.

As the most general method for detecting a double-stranded nucleic acid, known is a method for subjecting a solution after amplification reaction to Agarose electrophoresis, and applying the solution with fluorescent intercalators such as Ethidium Bromide or SYBR Green, and observing specific fluorescence (Non-Patent Document 1). However, a method for dyeing with fluorescent intercalators such as Ethidium Bromide after electrophoresis takes about 30 minutes to 1 hour for electrophoresis and needs expensive machines such as a UV irradiator or a fluorescent detector for detection of fluorescence.

As a method for detecting and determining a PCR product without performing electrophoresis, known is a method wherein fluorescent intercalators are added primarily to a reaction liquid before starting PCR, fluorescence intensity is measured with a fluorospectrophotometer, and the amount of amplified DNA is determined (Patent Document 1). However, since the fluorescent intercalators bind to single-stranded nucleic acid such as primer, a background signal which is independent of the amount of double-stranded nucleic acid is enhanced, resulting in reduction in detection sensitivity. In contrast, there is also known a method for reducing the intensity of background signals by treating compounds that preferentially react with intercalators bound to single-stranded nucleic acid (Patent Document 2). However, use of these methods involves devices and facilities for detecting fluorescence.

As a method other than the above methods, for example, known is a method for conducting nucleic acid amplification reaction with fluorescence-labeled primer, and detecting the nucleic acid amplification product with fluorescence polarization (Patent Document 3). However, the method needs a complicated operation for separating the fluorescence-labeled primer which was not incorporated into an amplification product, and the separation operation of the primer decrease the yield of the obtained nucleic acid amplification fragments, which may consequently cause reduction in detection sensitivity. Also, labeled nucleotide and labeled primer are usually very expensive in terms of cost.

Also known is a method for detecting a nucleic acid amplification product by passing polarized light through reaction liquid in nucleic acid amplification reaction and measuring the angle of rotation or circular dichroism of the polarized light (Patent Document 4). However, the measurement of angle of rotation and circular dichroism needs a special device.

Patent Document 1: Japanese Kokai Publication H5-237000
Patent Document 2: WO 2002/103053
Patent Document 3: Japanese Kokai Publication H9-187275
Patent Document 4: Japanese Kokai Publication 2002-186481
Non-Patent Document 1: Molecular Cloning second edition, vol. 1, 6.15 (1989)

SUMMARY OF THE INVENTION

The present invention has its object to provide a method, a device and kit for detecting a nucleic acid, which enable simple and precise visual detection of a nucleic acid amplified by a nucleic acid amplification method, without necessity of a special device.

As a result of earnest investigation to solve the above problems, the present inventors have found that when a dye whose color tone changes by binding to a nucleic acid is added before or after nucleic acid amplification reaction, observation with visible light enables detection of the presence of nucleic acid amplification. Further, the present inventors have found that addition of a substance that preferentially reacts with a dye bound to a single-stranded nucleic acid or a dye not bound to a nucleic acid, in comparison with a dye which binds to a double-stranded nucleic acid, enables change or removal of the color tone derived from dyes that does not bind to a double-stranded nucleic acid, and enables visual detection of the nucleic acid amplification fragment with simplicity and precision. Further, the present inventors have produced a kit or device for detecting a nucleic acid by eye using the present method, leading to completion of the present invention.

That is, the present invention relates to a method for detecting a nucleic acid in a sample, comprising the steps of: (1) contacting a sample with a dye to react with each other;

and (2) observing a substance produced by the reaction with visible light, and evaluating the presence of a nucleic acid by eye.

The detection method desirably further comprises a step of: (3) contacting a substance reactable with the dye with the sample, prior to or subsequent to the step (1).

The dye is desirably a dye whose color tone changes upon treating with an oxidizing agent, a reducing agent, an acid, a base, or a pH buffering agent.

The present invention also relates to a device or kit for detecting a nucleic acid in a sample, comprising: a carrier (a) that holds a dye which can bind to a nucleic acid; a path (c) for passing a sample through the carrier (a); and an evaluation part (d) for observing a substance produced by the reaction between the sample and the dye with visible light, and evaluating the presence of a nucleic acid by eye.

The device or kit desirably further comprises a carrier (b) that holds a substance reactable with a dye, the carrier (b) being disposed between the carrier (a) and the evaluation part (d).

The dye desirably comprises a dye whose color tone changes upon treating with an oxidizing agent, a reducing agent, an acid, a base, or a pH buffering agent.

The dye is desirably at least one dye selected from the group consisting of triphenylmethane dye, thiazine dye, oxazine dye, azine dye, xanthene dye, and phenanthridinium dye.

The dye is desirably at least one dye selected from the group consisting of Crystal Violet, Gentian Violet B, Victoria Blue B, Methyl Violet, Night Blue, Methyl Green, Toluidine Blue O, Azure B, Methylene Blue, Brilliant Cresyl Blue, Methyl Orange, Pyronin Y, Ethidium Bromide, and Neutral Red.

The substance reactable with a dye is desirably at least one compound selected from the group consisting of an oxidizing agent, a reducing agent, an acid, a base, and a pH buffering agent.

The acid is desirably at least one acid selected from the group consisting of hydrochloric acid, sulfuric acid, nitric acid, acetic acid, formic acid, oxalic acid, citric acid, and lactic acid.

The base is desirably at least one base selected from the group consisting of sodium hydroxide, potassium hydroxide, sodium bicarbonate, potassium carbonate, ammonia, and triethylamine.

The oxidizing agent is desirably at least one oxidizing agent selected from the group consisting of hydrogen peroxide, potassium permanganate, potassium chlorate, potassium dichromate, sodium bromate, potassium bromate, halogens, concentrated sulfuric acid, nitric acid, sodium hypochlorite, chlorine dioxide, chloramine, osmium tetroxide, dimethyl sulfoxide, and meta-chloroperbenzoic acid.

The reducing agent is desirably at least one reducing agent selected from the group consisting of sodium borohydride, sodium cyanoborohydride, sodium hydrogen sulfite, sodium sulfite, sodium hyposulfite, potassium pyrosulfite, sodium thiosulfate, glutathione, ascorbic acid, 2-mercaptoethanol, DL-dithiothreitol, 1-thioglycerol, cystein, tributyl phosphine, aminoethane thiol, and tris(2-carboxyethyl)phosphine.

The pH buffering agent is desirably at least one pH buffering agent selected from the group consisting of a Good's buffering solution, glycine, a phosphoric acid, a phthalic acid, a citric acid, a barbituric acid, a succinic acid, an acetic acid, and a carbonic acid.

The present invention also relates to a device or kit for detecting a nucleic acid, comprising: a carrier (e) that holds a dye which can bind to a nucleic acid and comprises an opening openable by external force to discharge the dye; a path (f) for introducing the discharged dye to the evaluation part (d) below; and an evaluation part (d) for holding the introduced sample, observing a substance with visible light, and evaluating the presence of a nucleic acid by eye, the substance being produced by the reaction between the dye introduced from the carrier (e) via the path (f), and the held sample.

A sample present in the evaluation part desirably further comprises another substance reactable with the dye.

The dye desirably comprises a dye whose color tone changes upon treating with an oxidizing agent, a reducing agent, an acid, a base, or a pH buffering agent.

Effects of the Invention

The method of the present invention enables visual detection of the presence of nucleic acid amplification by the change of color tone of a dye after nucleic acid amplification, without using a special detection device. Further, the change in color tone of a dye caused by an oxidizing agent, a reducing agent, an acid, a base, and a pH buffering agent enables visual detection of the presence of nucleic acid amplification. Detection with visible light provides a simple method for detecting a nucleic acid in the visible light region, using a spectrophotometer which is one kind of a highly versatile device.

BRIEF DESCRIPTION OF THE DRAWINGS

FIG. 1 is a schematic view illustrating an example of a chromatography type device for detecting a nucleic acid according to the present invention.

FIG. 2a and FIG. 2b each illustrates a filter type device.

FIG. 3 is a schematic view illustrating an example of a suction type device for detecting a nucleic acid of the present invention.

FIG. 4 is a schematic view illustrating an example of a channel type device for detecting a nucleic acid according to the present invention.

FIG. 5 is a schematic view illustrating an example of a tube type device for detecting a nucleic acid according to the present invention.

FIG. 6 is an absorption spectrography upon addition of Methyl Green to LAMP reaction liquid in Example 5.

FIG. 7 is an absorption spectrography upon addition of Methyl Green and then KOH to LAMP reaction liquid in Example 5.

FIG. 8 is an absorption spectrography upon addition of Toluidine Blue O to LAMP reaction liquid in Example 6.

FIG. 9 is an absorption spectrography upon addition of Toluidine Blue O and then sodium sulfite to LAMP reaction liquid in Example 6.

Hereinafter, the present invention will be described in detail.

1. Method for Detecting Nucleic Acid

The method for detecting a nucleic acid in a sample comprises the steps of: (1) contacting a sample with a dye to react with each other; and (2) observing a substance produced by the reaction with visible light, and evaluating the presence of a nucleic acid by eye.

In the step (1) of contacting a sample with a dye to react with each other, the way of contacting is not particularly limited as long as the contacting of a sample with a dye leads to some reaction therebetween.

In the present invention, the object to be detected is a nucleic acid, and examples of the double-stranded nucleic acid include a double-stranded DNA, a double-stranded RNA, a DNA-RNA hybrid chain, and a double strand of an artificial nucleic acid, such as PNA. Further, when a plurality of single-stranded nucleic acids are mixed, and coloration caused by a dye is possible, these can be detected by the detection method of the present invention.

The sample is not particularly limited as long as it contains a nucleic acid. Not only reaction liquids used in the nucleic acid amplification method, but also extracts from microorganisms, animal cells, or plant cells may be used, and extracts from food may also be suitably used.

The nucleic acid amplification method may be any method as long as it amplifies the nucleic acid sequence, as represented by PCR method. Examples of the nucleic acid amplification method other than PCR method include conventional methods such as LCR (Ligase Chain Reaction) method, SDA (Strand Displacement Amplification) method, RCA (Rolling Circle Amplification) method, CPT (Cycling Probe Technology) method, Q-Beta Replicase Amplification Technology method, ICAN (Isothermal and Chimeric primer-initiated Amplification of Nucleic Acids) method, LAMP (Loop-Mediated Isothermal Amplification of DNA) method, NASBA (Nucleic acid Sequence-based Amplification method), and TMA (Transcription mediated amplification method), and are not limited to these. Q-Beta Replicase Amplification Technology method, RCA method, NASBA method, SDA method, TMA method, LAMP method, ICAN method, etc. are methods in which amplification reaction is performed at a constant temperature, and other methods such as PCR method and LCR method are methods in which amplification reaction is performed by thermal cycling.

When RNA is reverse transcribed into DNA by reverse transcriptase, etc., and the aforementioned nucleic acid amplification method is used by employing the DNA as a template, RNA can be indirectly detected.

Examples of the dye used herein include triphenylmethane dye, thiazine dye, oxazine dye, azine dye, phenazine dye, xanthene dye, phenantridium dye, azo dye, lactone dye, sultone dye, indigoid dye, cyanine dye, oxonol dye, styryl dye, porphyrin dye, thioxanthene dye, squalium dye, croconium dye, azulenium dye, dithiol metal salt dye, naphthoquinone dye, anthraquinone dye, indophenol dye, coumarin dye, ketocoumarin dye, pyrylium salt dye, thiopyrylium salt dye, thiazole dye, quinoline dye, benzophenone dye, thiobenzophenone dye, and mixtures thereof.

Desirable dyes are triphenylmethane dye, thiazine dye, oxazine dye, azine dye, phenazine dye, xanthene dye, phenantridium dye, azo dye, indigoid dye, lactone dye, sultone dye, and mixtures thereof.

Triphenylmethane dye used herein is a dye having a structure represented by the following Formula 1 or 2.

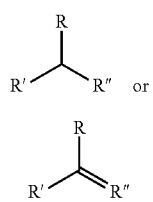

[Formula 1]

[Formula 2]

In the above Formula 1 or 2, R, R', and R" are each independently selected from substituted or unsubstituted aryl groups such as phenyl, naphthyl, and anthracenyl. The aryl group can be substituted with functional groups, such as amino, hydroxyl, carbonyl, carboxyl, sulfonic acid or alkyl, and/or other functional groups such as alkyl.

The dye usable for detecting a nucleic acid is not particularly limited as long as it can bind to a nucleic acid. Specific examples thereof include triphenylmethane dyes such as Methyl Green, Malachite Green, Crystal Violet, parafuchsin, Gentian Violet B, Gentian Violet R, Night Blue, Victoria Blue B, Victoria Blue R, Victoria Blue 4R, Victoria Blue BO, rosolic acid, fuchsin, acid fuchsin, basic fuchsin, new fuchsin, Bromothymol Blue, Bromocresol Green Phenolphthalein, Bromophenol Blue, Patent Blue Violet, Phenol Red, Pigment Blue 1, Pigment Violet 3, Benzyl Violet, pentamethyl parafuchsin, Fast Green FCF, Ethyl Violet, Green S, rosaniline, Acid Blue 7, Azure Blue G, Solochrome Cyanine R, Acid Blue 147, Light Green SF Yellow, Light Green SF, Ethyl Green, Aniline Blue, Methyl Violet, and Chromium Violet CG.

Examples of the thiazine dye include Toluidine Blue O, Methylene Blue, thionine, Azure A, and Thiol C.

Examples of the oxazine dye include Brilliant Cresyl Blue, Nile Blue, gallocyanine, and Basic Blue 3.

Examples of the azine dye include Aniline Black, and Acetylene Black.

Examples of the phenazine dye include Neutral Red, Janus Green B, Basic Red 2, and Safranine B.

Examples of the xanthene dye include Fluoresceine, Rhodamine and Pyronin Y.

Examples of the phenantridium dye include ethidium bromide.

Examples of the azo dye include Bismark Brown, New Coccin, and Basic Red 29.

Examples of the indigoid dye include indigo carmine.

The addition amount of a dye to a nucleic acid-containing solution is not particularly limited as long as the coloration of a solution can be observed by eye. The addition amount is desirably 1% or less, and more desirably 0.1% or less.

Of these dyes, dyes that have the property of the color tone changing upon binding to a nucleic acid and also have both acid-base reactivity and oxidation-reduction reactivity are desirable, and dyes may have the property of the color tone changing upon binding to a nucleic acid and also have either acid-base reactivity or oxidation-reduction reactivity. These dyes may be used singly, or two or more kinds thereof may be used in combination.

The dye whose color tone changes with the pH in a solution is referred to as an "acid-base responsive dye", and the dye whose color tone changes in the oxidation-reduction state is referred to as an "oxidation-reduction responsive dye." Examples of the oxidation-reduction responsive dye include a dye used for an acid-base indicator or an oxidation-reduction indicator.

Examples of the dye that has the property of the color tone changing upon binding to a nucleic acid include Toluidine Blue O, Methyl Green, Brilliant Cresyl Blue, Gentian Violet B, and Victoria Blue B. Specifically, Toluidine Blue O assumes navy blue without a double-stranded nucleic acid, and changes to light blue upon binding to a nucleic acid while Methyl Green assumes light blue without a nucleic acid, and changes to blue green upon binding to a nucleic acid. Brilliant Cresyl Blue assumes dark blue without a nucleic acid, and changes to blue green upon binding to a nucleic acid.

The acid-base responsive dye refers to a dye whose color tone changes according to the hydrogen-ion concentration (pH) in a solution, as seen in a pH indicator, etc. Of these, there may be mentioned a dye whose color tone changes from a solid color to red purple as in phenolphthalein, and a dye whose color tone change from red to orange as in Methyl Orange, when the solution changes from acidic to alkaline.

The oxidation-reduction responsive dye refers to a dye whose color tone changes in the oxidation state and the reduction state. For example, Methylene Blue and Methyl Green assume blue in the oxidation state, and change to a solid color in the reduction state. In contrast, Toluidine Blue O assumes blue in the oxidation state, and assumes red purple in the reduction state.

Upon detecting amplification of a nucleic acid by a nucleic acid amplification method, a dye is desirably added to the reaction liquid after the nucleic acid amplification reaction, or a dye may be added to the reaction liquid before the amplification reaction. The detection method of the present invention is also applicable to the detection of a nucleic acid not subjected to amplification reaction.

When an acid-base response dye or an oxidation-reduction responsive dye is used, addition of a step of adding a substance that preferentially reacts with a dye bound to a single-stranded nucleic acid and a dye not bound to a nucleic acid, in comparison with a dye which binds to a double stranded nucleic acid, enhances the contrast in color tone by the presence of a nucleic acid, and facilitates detection with visible light. That is, the contrast in color tone by the presence of a double-stranded nucleic acid is enhanced by changing the color tone derived from a dye bound to the other nucleic acids than a double-stranded nucleic acid, or diminish the color. As long as a dye has acid-base response or oxidation-reduction response, the above step enables visual evaluation of double-stranded nucleic acid amplification even upon using a dye that binds to a double-stranded nucleic acid but shows a little change in color tone caused by binding to the double-stranded nucleic acid or a dye that binds to a double-stranded nucleic acid but shows no change in color tone.

The change in color tone of Methyl Green, for example, is less likely to be evaluated by eye upon binding to a double-stranded nucleic acid. However, addition of a substance that preferentially reacts with Methyl Green bound to a single-stranded nucleic acid and Methyl Green not bound to a nucleic acid makes it possible to remove light blue derived from Methyl Green not bound to a double-stranded nucleic acid. This method facilitates visual evaluation of the presence of a nucleic acid such that a double-stranded nucleic acid exists when the sample is colored, and a double-stranded nucleic acid does not exist when the sample is colorless.

Another example is that when Toluidine Blue O binds to a double-stranded nucleic acid, it changes from navy blue to light blue. Further, addition of a substance that preferentially reacts with Toluidine Blue O bound to a single-stranded nucleic acid and Toluidine Blue O not bound to a nucleic acid makes it possible to change navy blue derived from Toluidine Blue not bound to a double-stranded nucleic acid into red purple. This method facilitates visual evaluation of the presence of a nucleic acid such that a double-stranded nucleic acid exists when the sample assumes blue, and a double-stranded nucleic acid does not exist when the sample assumes red purple.

Another example is that the change in color tone of Gentian Violet B is less likely to be evaluated by eye upon binding to a double-stranded nucleic acid. However, addition of a substance that preferentially reacts with Gentian Violet B bound to a single-stranded nucleic acid and Gentian Violet B not bound to a nucleic acid makes it possible to remove violet derived from Gentian Violet B not bound to a double-stranded nucleic acid. This method facilitates visual evaluation of the presence of a nucleic acid such that a double-stranded nucleic acid exists when the sample assumes violet, and a double-stranded nucleic acid does not exist when the sample is colorless.

Another example is that the change in color tone of Victoria Blue B is less likely to be evaluated by eye in a neutral solution upon binding to a double-stranded nucleic acid. However, Victoria Blue B-derived blue not bound to a double-stranded nucleic acid changes from blue to pale red in pH environments in the neutral or higher alkaline region. This method facilitates visual evaluation of the presence of a nucleic acid such that a double-stranded nucleic acid exists when the sample assumes blue, and a double-stranded nucleic acid does not exist when the sample assumes pale red.

When the effect of enhancing the contrast in color tone is to be obtained in this step, the dye to be used is not particularly limited. When not binding to a double-stranded nucleic acid, a dye that changes from colored to colorless or vice versa depending on pH or the oxidation-reduction state may be used. A dye whose color tone changes, for example, from blue to red may be used. The dye that changes from colored to colorless or vice versa depending on pH or the oxidation-reduction state is desirable because of easy evaluation of the presence of a nucleic acid.

Upon using the dye having oxidation-reduction response, there may be mentioned an oxidizing agent, a reducing agent, etc. as a substance that preferentially reacts with a dye bound to a single-stranded nucleic acid and a dye not bound to a nucleic acid, to change the color tone of the sample.

The oxidizing agent is not particularly limited as long as it has an oxidative effect, and examples thereof include hydrogen peroxide, potassium permanganate, potassium chlorate, potassium dichromate, sodium bromate, potassium bromate, halogens, concentrated sulfuric acid, nitric acid, sodium hypochlorite, chlorine dioxide, chloramine, osmium tetroxide, dimethyl sulfoxide, and meta-chloroperbenzoic acid.

The reducing agent is not particularly limited as long as it has a reducing effect, and examples thereof include sodium borohydride, sodium cyanoborohydride, sodium hydrogen sulfite, sodium sulfite, sodium hyposulfite, potassium pyrosulfite, sodium thiosulfate, glutathione, ascorbic acid, 2-mercaptoethanol, DL-dithiothreitol, 1-thioglycerol, cystein, tributyl phosphine, aminoethane thiol, tris(2-carboxyethyl)phosphine, and derivatives thereof.

When an acid-base responsive dye is used, an acid and a base can be used as a substance that preferentially reacts with a dye bound to a single-stranded nucleic acid and a dye not bound to a nucleic acid, to changes the color tone of the sample. Suitable examples of the acid include, but not limited thereto, inorganic acids, such as hydrochloric acid, sulfuric acid, and nitric acid, and organic acids, such as acetic acid, formic acid, oxalic acid, citric acid, and lactic acid. The acid is desirably hydrochloric acid, sulfuric acid, acetic acid, and citric acid, and particularly desirably hydrochloric acid and acetic acid. Suitable examples of the base include, but not limited thereto, sodium hydroxide, potassium hydroxide, sodium bicarbonate, potassium carbonate, ammonia, and triethylamine. The base is desirably sodium hydroxide, potassium hydroxide, and sodium bicarbonate, and particularly desirably sodium hydroxide and sodium bicarbonate.

A pH buffering agent is used as a substance that preferentially reacts with a dye bound to a single-stranded nucleic acid and a dye not bound to a nucleic acid, to change the color tone of the sample with the change in pH. The pH buffering agent is not particularly limited as long as it changes the pH of the sample, and suitable examples thereof include a Good's buffering solution, glycine, a phosphoric acid, a phthalic acid, a citric acid, a barbituric acid, a succinic acid, a citric acid, an acetic acid, and a carbonic acid, and specific examples thereof include MES, Bis-Tris, ADA, PIPES, ACES, MOPSO, BES, MOPS, TES, HEPES, DIPSO, TAPSO, POPSO, HEPPSO, EPPS, Tricine, Tris, Bicine, TAPS, CHES, CAPSO, and CAPS.

The specific addition amount of a substance that preferentially reacts with a dye bound to a single-stranded nucleic acid and a dye not bound to a nucleic acid to change the color tone of the sample, depends on the kind of a dye and the substance, and therefore cannot be uniformly defined. An ordinary person skilled in the art can experimentally determine the addition amount that most facilitates visual evaluation. Generally, the amount of the substance reactable with a dye is desirably 1000 mole equivalents or less of dye amount, and more desirably 100 mole equivalents or less.

When a nucleic acid amplification product is detected by this method, a dye may be added to a reaction liquid after a nucleic acid amplification reaction, and a substance that changes the color tone, such as an oxidizing agent, a reducing agent, an acid, a base, or a pH buffering agent, may be further added to the mixed liquid to enhance the contrast. Alternatively, an amplification reaction may be performed with the dye preliminarily added, and the oxidizing agent, the reducing agent, the acid, the base, etc. may be added after the reaction to enhance the contrast. The oxidizing agent, the reducing agent, the acid, the base, or the pH buffering agent may be used alone, or two or more kinds thereof may be used in combination. When the sample containing a nucleic acid originally contains the oxidizing agent, the reducing agent, the acid, the base, or the pH buffering agent, the nucleic acid can be detected only in the reaction step with the dye.

Subsequently, a substance produced by the reaction in the step (1) is observed with visible light. In the step (2) of evaluating the presence of a nucleic acid by eye, the substance is observed with visible light such as light in a general laboratory, instead of irradiating light, such as ultraviolet light, which is not visible. Visible light does not need a special device such as ultraviolet irradiator, but enables simple observation.

Visual evaluation by observation with visible light means visual observation of the change in coloration upon binding of a dye with a nucleic acid or of the change in coloration of the dye not bound to a nucleic acid. The presence of a nucleic acid can be observed based on the presence of the coloration of the dye under visible light.

Here, examples of the change in color tone include change in color with visible light (visible light wavelength) and change in color shade (reflectance), and are not limited to these as long as visual evaluation is possible. Examples of the change in color include change from red purple to light blue and change from yellow to red purple.

A nucleic acid is detectable by measuring the absorbance of the sample solution in the visible light range. The visible light used herein refers to light especially in the range of 380 nm to 800 nm. The measuring wavelength may be suitably adjusted based on a dye to be used. The absorbance measurement enables determination of the nucleic acid concentration in a sample.

In addition, upon producing an insoluble sediment from a dye and a nucleic acid, sediments may be collected by a filter or membrane or by centrifugation, to determine the amount of nucleic acid from the amount of sediment.

In the present invention, the colored sample liquid after detecting a nucleic acid may be used for other molecular biology operations. Examples of the molecular biology operations include restriction enzyme reaction, sequence reaction, enzyme reaction such as PCR, and confirmation by electrophoresis.

The detection method according to the present invention may further comprise a step of: (3) contacting, with the sample, a substance, such as an oxidizing agent, a reducing agent, an acid, a base, or a pH buffering agent, which is reactable with the dye, prior to or subsequent to the step (1).

2. Device or Kit for Detecting Nucleic Acid

A device or kit for detecting a nucleic acid according to the first embodiment of the present invention comprises: a carrier (a) that holds a dye which can bind to a nucleic acid; a path (c) for passing a sample through the carrier (a); and an evaluation part (d) for observing a substance produced by the reaction between the sample and the dye under visible light, and evaluating the presence of a nucleic acid by eye.

The material of the carrier (a) that holds a dye which can bind to a nucleic acid is not particularly limited as long as it can hold a dye, and a sample containing a nucleic acid can pass through it. Desirable specific examples thereof include nonwoven fabric, filter paper, glass fiber filter paper, glass cloth, glass filter, nitrocellulose filter, and a porous material made of polyethylene, polypropylene, or the like. The dye can be fixed to the carrier (a) by commonly known methods of physical adsorption or chemical bond. As physical adsorption, there may be mentioned dry adsorption in which a carrier is immersed in a predetermined amount of a dye solution and then dried.

The amount of the dye held by the carrier (a) is not particularly limited as long as the nucleic acid can be evaluated by eye. The dye concentration after mixing with a sample containing a nucleic acid is desirably 1% or less, and more desirably 0.1% or less.

When a sample passes through the carrier (a) that holds a dye, the dye binds to a nucleic acid. When the sample contains the nucleic acid, the sample contacts the dye to bind to each other. When the amount of the dye held by the carrier is excessive to the nucleic acid, a free dye remains. Here, examples of the binding includes covalent bond such as peptide bond and disulfide bond, ionic bond, coordinate bond, van der Waals bond, and noncovalent bond such as π-π interaction.

The binding of the nucleic acid to the dye in the carrier (a) is affected by compatibility of the nucleic acid with the carrier and hygroscopicity of the carrier. Accordingly, the surface of these carriers may be coated with a hydrophilic polymer or a surfactant, or these carriers may be immersed therein in order to adjust nonspecific adsorption of the nucleic acid and hygroscopicity of the carrier.

The path (c) in which a sample passes through the carrier (a) refers to a path in which the sample applied to the device or kit of the present invention moves. The path is not particularly limited as long as movement of a sample is derived, and a groove is not necessarily formed. The path (c) is connected to the carrier (a) and an evaluation part (d), and a sample is movable to the carrier (a) and the evaluation part (d) along the path (c). The material of the path (c) is not particularly limited as long as the sample containing a nucleic acid can pass through it.

The evaluation part (d) for observing a substance produced by the reaction between the sample and the dye with visible light, and evaluating the presence of a nucleic acid by eye, refers to a part in which the sample that has passed through the carrier (a) moves through the path (c) and reaches.

By observing the difference in color tone with visible light and thereby evaluating the coloration in the evaluation part (d), the presence of a nucleic acid can be evaluated without using a special device, such as an ultraviolet irradiation device and a fluorescence detector.

The material of the evaluation part (d) is not particularly limited as long as the sample containing a nucleic acid can pass through it or can be absorbed by it. Desirable specific examples thereof include nonwoven fabric, filter paper, glass fiber filter paper, glass cloth, glass filter, nitrocellulose filter, and a porous material made of polyethylene, polypropylene, or the like. These materials have advantages, such as a suitable moisture absorption speed, and excellent visual checking upon coloring and development of a nucleic acid.

Further, the correlation table showing the degree of coloration according to the amount of nucleic acid enables estimation of the nucleic acid concentration in a sample. The calibration curve prepared by using the standard nucleic acid with a specified concentration enables determination of the amount of nucleic acid in a sample by using a general analytical device, such as a spectrophotometer, a color difference meter, or a reflectometer.

The method for applying a sample to a device for detecting a nucleic acid of the present invention is not particularly limited, and the sample is applied by dropping, immersion, suction, or centrifugation, for example. The sample is added to the device and can be thereafter separately migrated with a solvent. Upon migration with a solvent, the solvent to be used is not particularly limited as long as it does not affect the color tone of the dye, and examples thereof include water, and a buffer solution. A sample addition part may be separately provided in the device for detecting a nucleic acid of the present invention. The sample may also be directly applied to the carrier (a) that holds a dye.

The aforementioned detection device or kit may further have a carrier (b) that holds a substance reactable with a dye. In this case, the carrier (b) is desirably located downstream of the carrier (a) that holds a dye. It is to be noted that the upstream and the downstream are relative directions; namely, the upstream is the side to which a sample is added, and the downstream is the side in which a sample flows or is migrated. The sample that reacts with a dye in the carrier (a) contacts a substance reactable with a dye in the carrier (b), and thereafter reaches the evaluation part (d) through the path (c).

The sample which contains the dye bound to a nucleic acid and a free dye contacts and mixed with a substance reactable with a dye in the carrier (b) that holds the substance reactable with a dye. Compared with the dye that binds to a nucleic acid, the free dye is highly reactive with the substance reactable with a dye, and therefore preferentially reacts and the color is changed. Change of color in this case means any change of color tone, and examples thereof include change from colored to clear and colorless, and change from red to blue.

Examples of a substance that is held by the carrier (b) and reactable with a dye include an oxidizing agent, a reducing agent, an acid, a base, and a pH buffering agent. The material of the carrier (b) is not particularly limited as long as it can hold a substance reactable with a dye and the sample containing a nucleic acid can pass through it.

The carriers (a) and (b) may or may not contact with each other. Another carrier may also be disposed between both of the carriers and/or in front and back of the carriers. If necessary, the device further comprises the region that applies a sample, the region that evaluates coloration, and the region that encourages mixing of the sample with a dye and the substance reactable with a dye. When the sample contains the substance reactable with a dye, the device or kit for detecting a nucleic acid according to the present invention may be composed only of the carrier that holds a dye.

When a dye, and a substance reactable with the dye, such as an oxidizing agent, are held by the same carrier, a device for detecting a nucleic acid can be produced by the one carrier. When the color tone of the dye can be changed with a compound derived from the sample such as a nucleic acid amplification reaction liquid, a device for detecting a nucleic acid having only a carrier (a) that holds a dye may be produced.

In the detection device of the present invention, the member to be used as the base material for disposing a carrier is not particularly limited as long as it can hold a carrier, and example thereof include a material such as plastic, paper, and glass. The member may have adhesiveness on its surface.

As thus described, in the device for detecting a nucleic acid according to the present invention, a step of binding a nucleic acid with a dye, and a step of enhancing the contrast in color tone by the presence of a nucleic acid can be simultaneously performed, and the nucleic acid can be detected rapidly and simply.

FIGS. 1 to 4 illustrate specific examples of a device for detecting a nucleic acid according to the present embodiment.

FIG. 1 illustrates a chromatography type device for detecting a nucleic acid. In FIG. 1, a carrier 1 that holds a dye which can bind to a nucleic acid, a carrier 2 that holds a substance reactable with a dye, a sample addition part 3, and an evaluation part 4 are pasted together on a member 5 used as abase material by using an adhesive, etc. to produce a detection device.

FIG. 2a illustrates a filter type device. The detection device illustrated in FIG. 2a comprises an evaluation part 4, a filter type carrier 2 that holds a substance reactable with a dye, and a filter type carrier 1 that holds a dye which can bind to a nucleic acid, these being disposed perpendicularly in this order. The device according to the present embodiment does not have a sample addition part, a sample is directly applied to the carrier 1 that holds a dye which can bind to a nucleic acid, and the sample is mixed with the dye in the carrier 1. Thereafter, the mixture of the sample with the dye is permeated perpendicularly and contacts a substance reactable with a dye in the carrier 2. The mixture of the sample, the dye, and the substance reactable with the dye permeates into the evaluation part 4, and the presence of a nucleic acid can be evaluated by eye according to the color tone in the evaluation part 4.

FIG. 2b also illustrates a filter type device. In the device of FIG. 2b, a sample is applied in a support material 6, and is received in a sample receiving container 7 while sequentially contacting a dye held by the carrier 1, and then a substance reactable with a dye held by the carrier 2. According to the above configuration, the presence or the amount of nucleic acid in a sample can be evaluated based on the color tone of the sample solution received in the sample receiving container 7. When a sample is allowed to pass through a filter type carrier by centrifugation, pressurization, etc., the presence or amount of nucleic acid can be evaluated very rapidly and simply.

FIG. 3 illustrates a suction type device. The detection device illustrated in FIG. 3 comprises a carrier 1 that holds a dye which can bind to a nucleic acid, a carrier 2 that holds a substance reactable with a dye, and a support material 8 made of a suction device. The carrier 1 that holds a dye which can bind to a nucleic acid is disposed in a position relatively close to a suction opening α of a suction device, and the carrier 2 that holds a substance reactable with a dye is disposed in a position relatively distant therefrom. FIG. 3 illustrates a chip for a micropipet as a support material made of a suction device. In this case, an upper opening β is equipped with a micropipeter, and a sample is sucked from the suction opening α. The present embodiment is not limited to the chip for a micropipet, and can be desirably used for pipettes, such as a Pasteur pipette and a Komagome pipette, a capillary tube, an injector, etc. According to this configuration, by sucking a sample with a suction device provided with each carrier, the presence of a nucleic acid can be detected by eye extremely rapidly and simply based on the color tone of the dye.

FIG. 4 illustrates a channel type device. In the channel type device illustrated in FIG. 4, a carrier 1 that holds a dye which can bind to a nucleic acid, and a carrier 2 that holds a substance reactable with a dye are disposed on a chip 9 which is cut to form a channel. This chip may comprise the structure aimed at nucleic acid refining and nucleic acid amplification, etc. In the detection device of the present embodiment, the sample applied to a sample addition part 10 passes through a channel 13, and the carriers 1 and 2, in this order, and finally reaches an evaluation part 4. The presence or amount of nucleic acid can be determined by observing the coloration in the evaluation part 4 under visible light and evaluating it by eye. The shape of the channel 13 is not particularly limited, and may be a straight line or a curve. As illustrated in FIG. 4, efforts can be made to ensure that a plurality of combinations of channels and carriers are held on a chip 9, and the difference of time for passage through the channel 13 for the sample to reach the evaluation part 4 is made based on the length of the channel. When the chip 9 has the structure aimed at nucleic acid amplification, the amplification amount of the nucleic acid can be varied according to the difference of time for passage of a sample, and nucleic acid can be gradually amplified, and its product can be detected.

A device or kit for detecting a nucleic acid according to the second embodiment of the present invention comprises: a carrier (e) that holds a dye which can bind to a nucleic acid and which comprises an opening openable by external force to discharge the dye; a path (f) for introducing the discharged dye to the evaluation part (d) below; and an evaluation part (d) for holding the introduced sample, observing a substance with visible light, and evaluating the presence of a nucleic acid by eye, the substance being produced by the reaction between the dye introduced from the carrier (e) via the path (f) and the held sample.

The material of the carrier (e) that holds a dye which can bind to a nucleic acid and comprises an opening openable by external force to discharge the dye is not particularly limited as long as it can hold a dye for a predetermined period of time. The carrier (e) is filled with a dye, and an opening that discharges the dye is usually closed. The dye is discharged only when the carrier (e) is opened by external force. Here, the external force is not particularly limited as long as it enables opening of a carrier, and examples thereof include depression with a finger and depression with a machine. The embodiment of opening by external force is not particularly limited, and examples thereof include fracture of a film that holds a dye. The device or kit of the present embodiment may comprise an acicular structure to facilitate opening of the carrier (e).

The path (f) for introducing the discharged dye to the evaluation part is a path through which the dye discharged from the carrier (e) passes. The shape and material of the path (f) is not particularly limited as long as a dye can pass therethrough. When the discharged dye falls with gravity and reaches the evaluation part (d), for example, the shape and material of the path (f) is not limited as long as it does not prevent the dye from falling.

As described in the device or kit for detecting a nucleic acid according to the first embodiment of the present invention, the evaluation part (d) is for holding the introduced sample, observing a substance with visible light, and evaluating the presence of a nucleic acid by eye, the substance being produced by the reaction between the dye introduced from the carrier (e) via the path (f) and the held sample.

FIG. 5 illustrates a specific example of the device for detecting a nucleic acid according to the present embodiment.

FIG. 5 illustrates a tube type device. Examples of this tube type device include a device having a structure for adding a dye to a nucleic acid solution by external physical action. In FIG. 5, for example, a dye 11 is kept by a film in a lid part of a tube 14, and the dye 11 is added dropwise to the lower part of the tube, for example, by fracturing the film by external physical action such as pushing with a finger via an acicular structure 12 attached to the lid, whereby a double-stranded nucleic acid in a sample of the lower part of the tube can be stained.

In the tube type device illustrated in FIG. 5, when a sample in the tube 14 beforehand contains a substance reactable with a dye, addition of the dye 11 dropwise to the lower part of the tube 14 by external force can enhance the contrast of coloration by the presence of the double-stranded nucleic acid extremely rapidly and simply.

The kit for detecting a nucleic acid used herein refers to a kit comprising various chemical reagents or appliances, as well as a unit for detection comprising a solution and/or a substance reactable with a dye, the solution containing a dye which binds to a nucleic acid. The kit to which the above-mentioned devices are added is also regarded as a kit. Examples of various chemical reagents include a primer for amplifying the target nucleic acid, a DNA polymerase, a buffer solution for nucleic acid amplification reaction, and restriction enzymes.

The colored sample liquid obtained by using these devices may be used for other molecular biology operations. Examples of the molecular biology operations include restriction enzyme reaction, sequence reaction, enzyme reaction such as PCR, and confirmation by electrophoresis.

A sample can be treated automatically, and a device for detecting a nucleic acid according to the present invention can be incorporated in a device for analyzing base sequence, etc. For example, the presence of a nucleic acid can be evaluated by incorporating the device for detecting a nucleic acid of the present invention in a device for refining or amplifying a nucleic acid, and only samples amplified or labeled by PCR can be surely sorted or analyzed by incorporating them in a DNA automatic analyzer.

EXAMPLES

Hereinafter, the present invention will be specifically described byway of examples. However, the technical scope of the present invention is not limited to these examples.

Example 1

Detection of Nucleic Acid Using Toluidine Blue O and Methyl Green

5 μl of 0.1% Toluidine Blue O or 5 μl of 0.2% Methyl Green was added to 100 μl of a PBS buffer solution (positive control) containing a salmon-derived nucleic acid at a concentration of 1 mg/ml or 100 μl of a PBS buffer solution (negative control) not containing a nucleic acid, and the change in color tone was observed by eye. Further, the liquid mixture was diluted at a ratio of 1:10, and thereafter maximum absorption wavelength in the visible light range was measured by a spectrophotometer (V630 produced by Jasco Corporation).

Table 1 shows the results.

TABLE 1

| Dye | Nucleic acid | Color tone | Maximum absorption wavelength |
|---|---|---|---|
| Toluidine Blue O | − | Dark blue | 630 nm |
| | + | Light blue | 645 nm |
| Methyl green | − | Light blue | 630 nm |
| | + | Blue green | 640 nm |

The difference in color tone caused by the presence of a nucleic acid was remarkable in any of the dyes, and visual evaluation was possible immediately after the addition. The maximum absorption wavelength shifted from 630 nm to 645 nm in Toluidine Blue O, and from 630 nm to 640 nm in Methyl Green.

Example 2

Detection of PCR Reaction Product Using Toluidine Blue O

By using pUC19 (produced by Takara Bio, Inc.) as a template, the following primer F:5'-GGAAACAGCTAT-GACCATGA-3' (SEQ ID NO: 1) and primer R:5'-CTAT-GCGGCATCAGAGCAG-3' (SEQ ID NO: 2) were designed so that PCR amplification causes amplification of about 330 base pairs.

15 pmol of the primer F, 15 pmol of the primer R, and 10 ng of pUC19 were filled into a 0.2-ml tube for PCR, and 100 μl of a PCR reaction liquid was prepared according to the description of an ExTaq PCR kit (produced by Takara Bio, Inc.). Then, the tube was set to a thermal cycler (GeneAmp PCR System (produced by Applied Biosystems)). Subsequently, the tube was thermally treated at 95° C. for 5 minutes, and the cycle of 95° C. for 30 seconds, 55° C. for 30 seconds, and then 72° C. for 30 seconds was repeated 35 times. The target amplification of about 330 bp was performed as positive control. The same reaction was performed without adding ExTaq DNA polymerase as negative control. 5 μl of 0.1% Toluidine Blue O was each added to 100 μl of a reaction liquid subjected to nucleic acid amplification by PCR method and 100 μl of a reaction liquid not subjected to nucleic acid amplification, and the color tone was observed by eye. Further, the liquid mixture was diluted at a ratio of 1:10, and the maximum absorption wavelength in the visible light range was measured by a spectrophotometer.

Table 2 shows the results.

TABLE 2

| PCR method | Color tone | Maximum absorption wavelength |
|---|---|---|
| − | Dark blue | 630 nm |
| + | Light blue | 645 nm |

Even upon use of a nucleic acid amplification reaction liquid by PCR method, the change in color tone of Toluidine Blue O was observed. The shift of the maximum absorption spectrum was also observed.

Example 3

Detection of LAMP Method Reaction Product Using Methyl Green

"Loopamp Salmonella detection reagent kit" (Eiken Chemical Co., Ltd.) was used to prepare a nucleic acid amplification reaction liquid by LAMP method. 10 μl of Control DNA Sal and 40 μl of Master Mix (prepared by mixing Reaction Mix. Sal and Bst DNA Polymerase separately at a volume ratio of 20:1) were mixed, reacted at 65° C. for 1 hour, and further reacted at 80° C. for 20 minutes to prepare a reaction liquid (positive control) in which a nucleic acid was amplified. 10 μl of Control DNA Sal and 40 μl of Reaction Mix. Sal were mixed, reacted at 65° C. for 1 hour, and further reacted at 80° C. for 20 minutes to prepare a reaction liquid (negative control) in which a nucleic acid was not amplified. 5 μl of 0.1% Methyl Green was each added to 50 μl of positive control and 50 μl of negative control. The color tone of the reaction liquid was measured by eye, and thereafter, the maximum absorption wavelength was measured with a spectrophotometer.

Table 3 shows the results.

TABLE 3

| LAMP method | Color tone | Maximum absorption wavelength |
|---|---|---|
| − | Light blue | 630 nm |
| + | Blue green | 640 nm |

When Methyl Green was added to a nucleic acid amplification reaction liquid by LAMP method, the change in color tone of the reaction liquid was observed by eye. The shift of the maximum absorption spectrum was also observed.

Example 4

Detection of PCR Reaction Product Using Methyl Green and Contrast Enhancement Effect by Sodium Sulfite A nucleic acid amplification reaction liquid by PCR was prepared in the same manner as in Example 2. 5 μl of 0.1% Methyl Green was each added to 50 μl of positive control and 50 μl of negative control The change in color tone was observed after further addition of 2 μl of 0.1% sodium sulfite to the mixture. Thereafter, the reaction liquid was diluted at a ratio of 1:10, and an absorption spectrum of 450 nm to 750 nm and an absorbance in the maximum absorption wavelength were measured.

Table 4 shows the results.

TABLE 4

| PCR method | Sodium sulfite | Color tone | Maximum absorption wavelength | Absorbance (640 nm) |
|---|---|---|---|---|
| − | − | Light blue | 630 nm | 0.193 |
| − | + | Solid color | — | 0.006 |
| + | − | Blue green | 640 nm | 0.695 |
| + | + | Blue green | 640 nm | 0.388 |

Negative control without nucleic acid amplification by PCR assumed light blue upon addition of a dye and a solid color upon the subsequent addition of sodium sulfite. In contrast, positive control with nucleic acid amplification by PCR assumed blue green even after addition of sodium sulfite and showed no change in color tone upon the addition of sodium sulfite. The positive control had an absorbance of 0.695, and the negative control had an absorbance of 0.193, at 640 nm before addition of sodium sulfite. The absorbance ratio of the positive control to the negative control was 3.60. The absorbance ratio after addition of sodium sulfite reached 64.7. As thus described, addition of a dye and then sodium sulfite made clear the difference in color tone by the presence of a nucleic acid, and facilitated visual evaluation. The detection by the dye took 1 minute or less.

By using a sample containing a nucleic acid colored with Methyl Green and sodium sulfite, electrophoresis, PCR, treatment with restriction enzyme, and sequence reaction were all favorably conducted.

Example 5

Detection of LAMP Method Reaction Product Using Methyl Green and Contrast Enhancement Effect by KOH A nucleic acid amplification reaction liquid by LAMP method was prepared in the same manner as in Example 3. 5 µl of 0.1% Methyl Green was each added to 50 µl of positive control and 50 µl of negative control. The change in color tone was observed after further addition of 2 µl of 1 N KOH to the mixture. Thereafter, the reaction liquid was diluted at a ratio of 1:10, and an absorption spectrum of 450 nm to 750 nm and an absorbance in the maximum absorption wavelength were measured.

Table 5, and FIGS. 6 and 7 show the results.

TABLE 5

| LAMP method | KOH | Color tone | Maximum absorption wavelength | Absorbance (640 nm) |
|---|---|---|---|---|
| − | − | Light blue | 630 nm | 0.176 |
| − | + | Solid color | — | 0.005 |
| + | − | Blue green | 640 nm | 0.679 |
| + | + | Blue green | 640 nm | 0.353 |

Negative control without nucleic acid amplification by LAMP method assumed light blue upon addition of a dye and a solid color upon the subsequent addition of KOH. In contrast, positive control with nucleic acid amplification by LAMP method assumed blue green even after the addition of KOH and showed no change in color tone upon the addition of KOH. The positive control had an absorbance of 0.679, and the negative control had an absorbance of 0.176, at 640 nm before the addition of KOH. The absorbance ratio of the positive control to the negative control was 3.86. The absorbance ratio after addition of KOH reached 70.6. As thus described, addition of a dye and then KOH made clear the difference in color tone by the presence of a nucleic acid, and facilitated visual evaluation. The detection by the dye took 1 minute or less.

Example 6

Detection of LAMP Method Reaction Product Using Toluidine Blue O and Contrast Enhancement Effect by Sodium Sulfite A nucleic acid amplification reaction liquid by LAMP method was prepared in the same manner as in Example 3. 2.5 µl of 0.1% Toluidine Blue O was each added to 50 µl of positive control and 50 µl of negative control. The change in color tone was observed after further addition of 2 µl of 0.1 M sodium sulfite to the mixture. Thereafter, the reaction liquid was diluted at a ratio of 1:10, and an absorption spectrum of 450 nm to 750 nm and an absorbance in the maximum absorption wavelength were measured.

Table 6, and FIGS. 8 and 9 show the results.

TABLE 6

| LAMP method | Sodium sulfite | Color tone | Maximum absorption wavelength | Absorbance (645 nm) |
|---|---|---|---|---|
| − | − | Dark blue | 630 nm | 0.586 |
| − | + | Red purple | 630 nm | 0.119 |
| + | − | Light blue | 645 nm | 0.505 |
| + | + | Light blue | 645 nm | 0.513 |

Negative control assumed dark blue upon addition of a dye and red purple upon the subsequent addition of sodium sulfite. In contrast, positive control showed little change in color tone upon addition of sodium sulfite and assumed light blue. The positive control had an absorbance of 0.505, and the negative control had an absorbance of 0.586, at 645 nm before the addition of sodium sulfite. The absorbance ratio of the positive control to the negative control was 0.86. The absorbance ratio after addition of sodium sulfite reached 4.31.

As thus described, addition of a dye and then sodium sulfite made clear the difference in color tone by the presence of a nucleic acid, and facilitated visual evaluation. The detection by the dye took 1 minute or less.

Example 7

Detection of LAMP Method Reaction Product Using Pyronin Y and Contrast Enhancement Effect by Sodium Sulfite The same experiment as in Example 6 was conducted, except that Pyronin Y was used as a dye. The color tone was observed by eye, and an absorbance in the maximum absorption wavelength (560 nm) was measured.

Table 7 shows the results.

TABLE 7

| LAMP method | Sodium sulfite | Color tone | Maximum absorption wavelength | Absorbance (560 nm) |
|---|---|---|---|---|
| − | − | Red purple | 545 nm | 0.288 |
| − | + | Pale red | 545 nm | 0.086 |
| + | − | Red purple | 560 nm | 0.212 |
| + | + | Red purple | 560 nm | 0.18 |

Negative control assumed red purple upon addition of a dye and pale red upon the subsequent addition of sodium sulfite. In contrast, positive control showed little change in color tone upon addition of sodium sulfite. The positive control had an absorbance of 0.212, and the negative control had an absorbance of 0.288, at 560 nm before addition of sodium sulfite. The absorbance ratio of the positive control to the negative control was 0.74. The absorbance ratio after addition of sodium sulfite reached 2.09. Addition of a dye and then sodium sulfite made clear the difference in color tone by the presence of a nucleic acid, and facilitated visual evaluation. The detection by the dye took 1 minute or less.

Example 8

Detection of LAMP Method Reaction Product Using Neutral Red and Contrast Enhancement Effect by KOH The same experiment as in Example 6 was conducted, except that Neutral Red was used as a dye and KOH was used instead of sodium sulfite. The color tone was observed by eye, and an absorbance in the maximum absorption wavelength (525 nm) was measured.

Table 8 shows the results.

TABLE 8

| LAMP method | KOH | Color tone | Maximum absorption wavelength | Absorbance (525 nm) |
| --- | --- | --- | --- | --- |
| − | − | Red | 530 nm | 0.729 |
| − | + | Yellow | 530 nm | 0.322 |
| + | − | Red purple | 525 nm | 0.496 |
| + | + | Red purple | 525 nm | 0.581 |

Consequently, negative control assumed red upon addition of a dye and yellow upon the subsequent addition of KOH. In contrast, positive control showed little change in color tone upon addition of KOH. The positive control had an absorbance of 0.496, and the negative control had an absorbance of 0.729, at 525 nm before addition of KOH. The absorbance ratio of the positive control to the negative control was 0.680. The absorbance ratio after addition of KOH reached 1.80. Addition of a dye and the subsequent KOH treatment make clear the difference in color tone by the presence of a nucleic acid, and facilitated visual evaluation. The detection by the dye took 1 minute or less.

Example 9

Effect of Reducing Agent Exerted on Detection of LAMP Method Reaction Product by Methyl Green As a reducing agent, sodium ascorbate, glutathione, DL-dithiothreitol, 2-mercaptoethanol, or sodium thiosulfate was used instead of sodium sulfite to make the same experiment as in Example 5. The color tone was observed by eye.

Table 9 shows the results.

Here, the same experiment was made by adding sodium hydroxide to observe the color change by addition of alkali.

TABLE 9

| Reducing agent | Without nucleic acid amplification | With nucleic acid amplification |
| --- | --- | --- |
| None | Light blue | Blue green |
| Sodium hydroxide | Solid color | Blue green |
| Ascorbic acid | Pale blue | Blue green |
| Glutathione | Solid color | Blue green |
| DL-dithiothreitol | Solid color | Blue green |
| 2-Mercaptoethanol | Solid color | Blue green |
| Sodium thiosulfate | Solid color | Blue green |

Consequently, addition of all the reducing agents induces change in color tone of a reaction liquid not subjected to nucleic acid amplification, resulting in contrast enhancement.

Example 10

Detection of PCR Product by Dye

A nucleic acid amplification reaction liquid by PCR was prepared in the same manner as in Example 2. Various dyes were added to 50 µl of positive control and 50 µl of negative control so as to give a final concentration of 0.01 to 0.1%. Thereafter, an appropriate amount of a reducing agent (sodium sulfite), an oxidizer (hydrogen peroxide), an acid (hydrochloric acid), or a base (sodium hydroxide) was added to the mixture, and a test for detecting amplification nucleic acid was performed by eye.

Consequently, when parafuchsin, Basic Green 1, Basic Blue 3, Night Blue, Gentian Violet B, Eriochrome Cyanine R, Ethyl Violet, Methyl Violet, Astrazone Pink FG, Malachite Green, Crystal Violet, Victoria Blue B, Victoria Blue R, Victoria Blue 4R, basic fuchsin, or new fuchsin was used as a dye, addition of a dye and then a reducing agent made clear the difference in color tone by the presence of nucleic acid amplification, and enabled visual evaluation.

When pinacyanol or parafuchsin was used as a dye, addition of a dye and then an oxidizing agent made clear the difference in color tone by the presence of nucleic acid amplification, and enabled visual evaluation.

When pinacyanol, Janus Green B, parafuchsin, Basic Blue 7, Ethyl Violet, Victoria Blue R, basic fuchsin, new fuchsin, Methyl Violet, or Thiazole Orange was used as a dye, addition of a dye and then an acid made clear the difference in color tone by the presence of nucleic acid amplification, and enabled visual evaluation.

When carmine, proflavine sulfate, Azure A, thionine, parafuchsin, Basic Red 29, Basic Green 1, Astrazone Pink FG, Malachite Green, Crystal Violet, Victoria Blue 4R, Victoria Blue R, basic fuchsin, new fuchsin, Gentian Violet B, Night Blue, Basic Blue 7, Ethyl Violet, Methyl Violet, or Victoria Blue B was used as a dye, addition of the dye and then a base made clear the difference in color tone by the presence of nucleic acid amplification, and enabled visual evaluation.

Example 11

Detection of Nucleic Acid Using Victoria Blue B

2 µl of 0.01% of Victoria Blue B was added to 100 µl of a Tris-HCl buffer solution (positive control) having various pHs and containing a salmon-derived nucleic acid at a concentration of 1 mg/ml or 100 µl of a Tris-HCl buffer solution (negative control) having various pHs and not containing a nucleic acid, and the change in color tone was observed by eye.

Table 10 shows the results.

TABLE 10

| | pH | | | | | | | |
|---|---|---|---|---|---|---|---|---|
| | 6.5 | 7 | 7.5 | 8 | 8.5 | 9 | 9.5 | 10 |
| Negative control | Blue | Blue | Blue | Blue | Light purple | Pale red | Pale red | Pale red |
| Positive control | Blue | Blue | Blue | Blue | Blue | Blue | Blue | Blue |
| Visual evaluation | Impossible | Impossible | Impossible | Impossible | Possible | Possible | Possible | Possible |

Use of a pH buffer solution higher than pH 8.0 enabled visual evaluation immediately after the addition based on the difference in color tone caused by the presence of a nucleic acid. Upon use of a pH buffer solution having a pH of 8.5 to 9.5, the difference in color tone caused by the presence of a nucleic acid was more remarkable. Use of Night Blue in the same experiment also enabled visual evaluation immediately after the addition based on the difference in color tone caused by the presence of nucleic acid.

Example 12

Detection of PCR Reaction Product Using Victoria Blue B

A nucleic acid amplification reaction liquid (pH 8.8) by ExTaq PCR was prepared in the same manner as in Example 2. 1 µl of 0.01% Victoria Blue B was each added to 50 µl of positive control and 50 µl of negative control to observe change in color tone.

Consequently, negative control without nucleic acid amplification by PCR assumed light red upon addition of a dye. In contrast, positive control with nucleic acid amplification by PCR assumed blue upon addition of a dye. As thus described, addition of a dye made clear the difference in color tone by the presence of nucleic acid amplification, and facilitates visual evaluation. The detection by the dye took 1 minute or less.

By using a sample containing a nucleic acid colored with Victoria Blue B, electrophoresis, PCR, treatment with restriction enzyme, and sequence reaction were all favorably conducted.

Example 13

Production of Chromatography Type Device for Detecting Nucleic Acid
(1) Production of Carrier that Holds Dye which can Bind to Nucleic Acid 50 µl of 0.1% Methyl Green aqueous solution was immersed in a band-like cellulose filter paper (SureWick C068 produced by Millipore Corp.) with a width of 5 mm and length of 9 mm, and dried at room temperature to produce a carrier that holds a dye which can bind to a nucleic acid.
(2) Production of Carrier that Holds Substance Reactable with Dye 50 µl of 0.1% sodium sulfite aqueous solution was immersed in a band-like cellulose filter paper (SureWick C048 produced by Millipore Corp.) with a width of 5 mm and length of 9 mm, and dried at room temperature to produce a carrier that holds a substance reactable with a dye.
(3) Assembly of Chromatography Type Device A sample addition part of a glass fiber filter (SureWick G028 produced by Millipore Corp.) with a width of 5 mm and a length of 15 mm, an evaluation part of a cellulose filter paper (CFSP22300 produced by Millipore Corp.) with a width of 5 mm and a length of 20 mm were prepared in addition to both of the carriers. These carriers and parts were disposed on a PVC base material stuck with an adhesive sheet so that one end of each of these was overlapped by 1 mm in the same manner as in FIG. 1. Thereby, a chromatography type device for detecting a nucleic acid was produced.

Example 14

Detection of Nucleic Acid by Chromatography Type Device for Detecting Nucleic Acid A nucleic acid amplification reaction liquid by PCR was prepared in the same manner as in Example 2. The same reaction was performed without adding ExTaq DNA polymerase to produce negative control.

After 400 µl 20 mM Tris-HCl (pH 8.0) was added to each of the samples 100 µl, the liquid mixture was added dropwise with a micropipette to the sample addition part of the device produced in Example 13. The color tone of the evaluation part was observed by eye after 10-minute standing at room temperature. Table 11 shows the results.

TABLE 11

| | Example 14 | | Comparative Example 1 | |
|---|---|---|---|---|
| PCR method | + | – | + | – |
| Color tone | Blue green | White | Blue green | Blue green |
| Visual evaluation | Possible | | Impossible | |

"–" in the line of "PCR method" indicates negative control.
"+" in the line of "PCR method" indicates positive control.

With nucleic acid amplification by PCR method, an evaluation part assumes blue green. In contrast, without nucleic acid amplification, the color of a dye disappeared and assumed white (the color of a filter paper), and the presence of a nucleic acid was easily evaluated based on coloration of the evaluation part.

Comparative Example 1

A device was produced in the same manner as in Example 13, except that sodium sulfite was not immersed in the carrier that holds a substance reactable with a dye. Table 11 shows the results.

The evaluation part assumed blue green irrespective of the presence of nucleic acid amplification by PCR method, and the presence of a nucleic acid was difficult to evaluate by eye.

Example 15

Production of Filter Type Device for Detecting Nucleic Acid
(1) Production of Carrier that Holds Dye which Can Bind to Nucleic Acid A glass fiber filter paper (GA100 produced by ADVANTEC Co., Ltd.) was punched into a circle shape using a 6-mm punch. 50 µl of 0.1% Malachite Green aqueous solution was immersed in the obtained circular filter paper, and dried at room temperature to produce a carrier that holds a dye which can bind to a nucleic acid.

(2) Production of Carrier that Holds Substance Reactable with Dye

A glass fiber filter paper (GA100 produced by ADVANTEC Co., Ltd.) was punched into a circle shape using a 6-mm punch. 50 µl of 0.01% sodium sulfite aqueous solution was immersed in the obtained circular filter paper, and dried at room temperature to produce a carrier that holds a substance reactable with a dye.

(3) Assembly of Filter Type Device

The carrier that holds a substance reactable with a dye, and the carrier that holds a dye which can bind to a nucleic acid were disposed in this order on a cartridge having a shape illustrated in 6 of FIG. 2b. The cartridge on which the carriers were disposed was set to a microtube to produce a filter type device.

Example 16

Detection of Nucleic Acid by Filter Type Device for Detecting Nucleic Acid

A nucleic acid amplification reaction liquid by PCR was prepared in the same manner as in Example 2. The same reaction was performed without adding ExTaq DNA polymerase to produce negative control. Each of the samples 250 µl was added dropwise with a micropipette to the cartridge part of the device produced in Example 15. Thereafter, the sample was centrifuged (at 10,000 rpm for 10 seconds), and the color tone of the sample accumulating on the microtube was observed by eye. Table 12 shows the results.

TABLE 12

|  | Example 16 | |
| --- | --- | --- |
| Nucleic acid | + | − |
| Color tone | Blue | Solid color |
| Visual evaluation |  | Possible |

"−" in the line of "nucleic acid" indicates negative control.
"+" in the line of "Nucleic acid" indicates positive control.

The color tone of the sample solution changes to a blue or solid color by the presence of nucleic acid amplification, and visual evaluation was easily made.

Example 17

Assembly of Suction Type Device for Detecting Nucleic Acid (1) Production of Carrier that Holds Dye which Can Bind to Nucleic Acid 2 µl of 10% Methyl Green was immersed in a porous polyethylene sheet (pore diameter: 50 µm, thickness: 1.5 mm, diameter: 1.5 mm) punched into a circle shape, and dried at room temperature to produce a carrier that holds a dye which can bind to a nucleic acid.

(2) Production of Carrier that Holds Substance Reactable with Dye

2 µl of 1% sodium sulfite aqueous solution was immersed in a porous polyethylene sheet (pore diameter: 50 µm, thickness: 1.5 mm, diameter: 1.5 mm) punched into a circle shape, and dried at room temperature to produce a carrier that holds a substance reactable with a dye.

(3) Assembly of Suction Type Device

The carrier that holds a dye which can bind to a nucleic acid, and the carrier that holds a substance reactable with a dye were filled in this order into the pipette tip at the end of the pipette tip for 200 µl, as illustrated in FIG. 3.

Example 18

Detection of PCR Product Using Suction Type Device for Detecting Nucleic Acid

PCR reaction was performed in the same manner as in Example 2 to prepare positive control and negative control. The suction type device produced in Example 17 was attached to a micropipette, each of the samples 100 µl were sucked with the suction type device, and the color tone of the sample solution in the pipette tip was observed.

Table 13 shows the results.

TABLE 13

| PCR method | + | − |
| --- | --- | --- |
| Color tone | Blue green | Clear and colorless |

"−" in the line of "PCR method" indicates negative control.
"+" in the line of "PCR method" indicates positive control.

With nucleic acid amplification by PCR reaction, a sample liquid in a tip assumed blue green. In contrast, it assumed a solid color without nucleic acid amplification. It took only several seconds to detect an amplification nucleic acid using a suction type device, and rapid and simple visual evaluation was possible. When the PCR reaction was performed again using 1 µl of the sample liquid after evaluating nucleic acid amplification by a suction type device, the target nucleic acid was precisely amplified from the colored nucleic acid sample.

Example 19

Detection of Low-Concentration Nucleic Acid Using Suction Type Device for Detecting Nucleic Acid PCR reaction was performed in the same manner as in Example 2 to produce a reaction liquid containing 160 ng/µl of an amplification nucleic acid. The liquid mixture was diluted at a ratio of 1:2 (80 ng/µl), 1:4 (40 ng/µl), 1:8 (20 ng/µl), and then 1:16 (10 ng/µl) to prepare samples, each of which was then sucked with a pipette tip produced in Example 17.

Consequently, an amplification nucleic acid and a low-concentration nucleic acid were detected by eye in all the samples.

Example 20

Detection of Colony PCR Product Using Suction Type Device for Detecting Nucleic Acid Plasmid vector pUC19 for *Escherichia coli* (produced by Takara Bio, Inc.) was introduced to *Escherichia coli* JM109 (produced by Takara Bio, Inc.) based on the protocol attached to JM109. The *Escherichia coli* colony to which the vector was introduced was raised at 37° C. for 24 hours on the LB agar containing ampicillin at a concentration of 100 µg/ml. The colony was stabbed with a toothpick and suspended in 10 µl of sterilized water. PCR reaction was performed in the same manner as in Example 2 by using 1 µl of this sterilized water. When the reaction liquid after the PCR was sucked up by the pipette tip produced in Example 17, it assumed blue. The blue reaction liquid was subjected to 1.0% Agarose electrophoresis, and the amplification nucleic acid was surely observed. When the *Escherichia coli* to which the vector was not introduced was subjected to PCR as control samples, neither amplified nucleic acid nor coloration was observed.

Example 21

Examination of Feasible Treatment Using Sample After Detection

The amplified nucleic acid in the reaction solution obtained by the same PCR reaction as in Example 2 was detected by using the pipette tip produced in Example 17. By using a sample containing a colored nucleic acid after the detection, electrophoresis, PCR, treatment with restriction enzyme, and sequence reaction were conducted.

The result of electrophoresis showed that the mobility of the samples colored by a pipette tip for detecting a nucleic acid was the same as that of untreated samples and electrophoresis was possible even after the detection. When the same PCR reaction as in Example 2 was performed by using the detected 1 µl reaction solution as a template, it was possible to amplify the target sequence. When a treatment with restriction enzyme was performed on the detected samples, the enzyme reaction was not inhibited but the detected sample was cut. Similarly, when sequence reaction was performed by using the detected 1 µl reaction solution as a template, it was also possible to determine the base sequence.

Example 22

Device Capable of Detecting Nucleic Acid by Centrifuging After Amplification Reaction 100 µl of LAMP method reaction liquid was prepared by the same method as in Example 3 and transferred to a microtube part of Ultrafree-MC (PVDF film, 0.45 µm, produced by Millipore Corp.). Further, 50 µl of 0.001% Victoria Blue B solution was added to the upper part of the Ultrafree-MC filter cartridge. Then, after one-hour reaction at 65° C., a reaction liquid (positive control) in which a nucleic acid was amplified was prepared.

The reaction vessel was centrifuged (at 10,000 rpm for 1 minute) after amplification reaction, and thereby Victoria Blue B on the upper part of the filter cartridge was added dropwise to a microtube part. Consequently, a reaction solution was colored without opening and closing the lid of the reaction vessel, only upon nucleic acid amplification, which enabled evaluation of the presence of nucleic acid amplification.

Example 23

Detection of Nucleic Acid by Microchannel Type Device

From upstream on the channel, methyl Green-containing beads and reducing agent-containing beads were incorporated to produce a microchannel device having a form illustrated in FIG. 4. When nucleic acid amplification reaction was performed in the microchannel type device, the reaction liquid assumed blue after a sample solution passing through both of the beads. In contrast, when nucleic acid amplification was not performed in the microchannel type device, the reaction liquid assumed a transparent color after the sample solution passing through the beads, which enabled easy visual evaluation of nucleic acid amplification.

Example 24

Detection of Nucleic Acid by Tube Type Device

A needle was fixed to the lid part of a PCR tube (produced by Eppendorf Co., Ltd.), 10 µl of 0.01% Victoria Blue B solution used in Example 12 was added to the lid part, and Victoria Blue B was sealed with a commercially available filter to prepare a tube type device illustrated in FIG. 5. Nucleic acid amplification reaction by LAMP method was performed in the same manner as in Example 3 by using this tube. The lid was pressed down after the reaction to open a hole in a film with the needle. When Victoria Blue B solution was added to the reaction liquid, nucleic acid amplification was observed.

Example 25

Detection of PCR Reaction Product Using Gentian Violet B

A nucleic acid amplification reaction liquid by PCR was prepared in the same manner as in Example 2. 1.5 µl of 0.1% Gentian Violet B was each added to 50 µl of positive control and 50 µl of negative control. The change in color tone was observed after further addition of 1.5 µl of 1% sodium sulfite. The absorbance at 590 nm was measured.

Table 14 shows the results.

TABLE 14

| PCR | Sodium sulfite | Color tone | Absorbance (590 nm) |
|---|---|---|---|
| − | − | Violet | 1.255 |
|  | + | Solid color | 0.144 |
| + | − | Violet | 0.959 |
|  | + | Violet | 0.871 |

"−" in the line of "PCR" indicates negative control.
"+" in the line of "PCR" indicates positive control.

Negative reaction without nucleic acid amplification by PCR assumed violet upon addition of a dye and a solid color upon the subsequent addition of sodium sulfite. In contrast, positive control with nucleic acid amplification by PCR assumed violet even after addition of sodium sulfite and showed no change in color tone upon the addition of sodium sulfite. The positive control had an absorbance of 0.959, and the negative control had an absorbance of 1.255, at 590 nm before addition of sodium sulfite. The absorbance ratio of the positive control to the negative control was 0.76. The absorbance ratio after addition of sodium sulfite reached 6.04. As thus described, addition of a dye and then sodium sulfite made clear the difference in color tone by the presence of a nucleic acid, and facilitated visual evaluation. The detection by the dye took 1 minute or less.

By using a sample containing a nucleic acid colored with Gentian Violet B and sodium sulfite, electrophoresis, PCR, treatment with restriction enzyme, and sequence reaction were all favorably conducted.

Example 26

Detection of LAMP Method Reaction Product Using Gentian Violet B

A nucleic acid amplification reaction liquid by LAMP method was prepared in the same manner as in Example 3. 1.5 µl of 0.1% Gentian Violet B was each added to 50 µl of positive control and 50 μl of negative control. The change in color tone was observed after further addition of 1.5 μl of 1% sodium sulfite.

Negative control assumed violet upon addition of a dye and a solid color upon the subsequent addition of sodium sulfite. In contrast, positive control showed no change in color tone upon addition of sodium sulfite and assumed violet. As thus described, addition of Gentian Violet B and then sodium sulfite made clear the difference in color tone by the presence of a nucleic acid, and facilitated visual evaluation. The detection by the dye took 1 minute or less.

Example 27

Detection of PCR Product with Gentian Violet B and Sodium Sulfite Using Suction Type Device for Detecting Nucleic Acid A suction type device was produced by the same method as in Example 17, except Gentian Violet B was used for a carrier that holds a dye which can bind to a nucleic acid. PCR reaction was performed in the same manner as in Example 2, positive control and negative control were prepared, each of the samples 100 μl were sucked with a suction type device, and the color tone of the sample solution in the pipette tip was observed.

Table 15 shows the results.

TABLE 15

| PCR method | + | − |
|---|---|---|
| Color tone | Violet | Clear and colorless |

"−" in the line of "PCR method" indicates negative control.
"+" in the line of "PCR method" indicates positive control.

With nucleic acid amplification by PCR reaction, a sample liquid in a tip assumed violet. In contrast, it assumed a solid color without nucleic acid amplification. It took only several seconds to detect an amplification nucleic acid using a suction type device, and rapid and simple visual evaluation was possible. When the PCR reaction was performed again using 1 μl of the sample liquid after evaluating nucleic acid amplification by a suction type device, the target nucleic acid was normally amplified from the colored nucleic acid sample.

EXPLANATION OF SYMBOLS

1. Carrier that holds dye which can bind to nucleic acid
2. Carrier that holds substance reactable with dye
3. Sample addition part (glass fiber filter paper)
4. Evaluation part (filter paper)
5. Base material
6. Support material that holds carrier
7. Sample receiving container
8. Pipette tip
9. Tip having channel
10. Sample addition part
11. Dye
12. Acicular structure
13. Channel
14. Tube

The invention claimed is:

1. A method for evaluating whether a double-stranded nucleic acid is present in a sample, comprising the steps of:
   (1) forming a solution by contacting a sample with a dye, wherein said double-stranded nucleic acid and said dye react with each other if said double-stranded nucleic acid is present in said sample; and wherein the amount of said dye in the sample is 1% or less than 1% such that a color of the solution, which is produced by interacting said amount of said dye with said double-stranded nucleic acid if said double-stranded nucleic acid is present in said sample or is produced by said amount of said dye itself if said double-stranded nucleic acid is absence in said sample, can be evaluated by eye with visible light;
   (2) subsequent to step (1), adding a substance reactable with the dye into the solution in an amount of 1000 mole equivalents or less than 1000 mole equivalents of the amount of the dye and wherein said amount of said substance facilitates visual evaluation, said substance is a reducing agent and can change the color of a solution comprising a single-stranded nucleic acid and the dye by binding said substance to the dye in a complex formed by the single-stranded nucleic acid and the dye or change the color of a solution consisting of the dye by binding said substance to the dye, and cannot cause the color change of the dye in a solution comprising a double-stranded nucleic acid and the dye by binding said substance to the dye in a complex formed by the double-stranded nucleic acid and the dye, and (3) observing the color of the solution by eye with visible light after step (2) and evaluating whether said double-stranded nucleic acid is present in a sample based on the color of the solution, wherein the reducing agent is an agent selected from the group consisting of sodium borohydride, sodium cyanoborohydride, sodium hydrogen sulfite, sodium sulfite, sodium hyposulfite, potassium pyrosulfite, sodium thiosulfate, glutathione, ascorbic acid, 2-mercaptoethanol, DL-dithiothreitol, 1-thioglycerol, cystein, tributyl phosphine, aminoethane thiol, and tris(2-carboxyethyl)phosphine, and wherein the dye is selected from the group consisting of triphenylmethane dye, Toluidine Blue O and Neutral Red.

2. The method according to claim 1, wherein said 1% or less than 1% is 0.1% or less than 0.1%.

3. The method according to claim 1, wherein the amount of 1000 mole equivalents or less than 1000 mole equivalents of the amount of the dye is 100 mole equivalents or less than 100 mole equivalents of the amount of the dye.

4. The method according to claim 1, wherein the triphenylmethane dye is selected from the group consisting of Methyl Green, parafuchsin, Night Blue, Gentian Violet B, Eriochrome Cyanine R, Ethyl Violet, Methyl Violet, Malachite Green, Crystal Violet, Victoria Blue B, Victoria Blue R, Victoria Blue 4R, basic fuchsin, and new fuchsin.

* * * * *

SEQUENCE LISTING

```
<160> NUMBER OF SEQ ID NOS: 2

<210> SEQ ID NO 1
<211> LENGTH: 20
<212> TYPE: DNA
<213> ORGANISM: Artificial
<220> FEATURE:
<223> OTHER INFORMATION: Synthetic primer

<400> SEQUENCE: 1
ggaaacagct atgaccatga                                          20

<210> SEQ ID NO 2
<211> LENGTH: 19
<212> TYPE: DNA
<213> ORGANISM: Artificial
<220> FEATURE:
<223> OTHER INFORMATION: Synthetic primer

<400> SEQUENCE: 2
ctatgcggca tcagagcag                                           19
```